United States Patent [19]

Nakamura et al.

[11] Patent Number: 5,180,798
[45] Date of Patent: Jan. 19, 1993

[54] PROCESS FOR PRODUCTION OF WATER-ABSORBENT RESIN

[75] Inventors: Morio Nakamura; Takushi Yamamoto, both of Kakogawa; Hitoshi Tanaka, Himeji; Hitoshi Ozawa, Himeji; Yasuhiro Shimada, Himeji, all of Japan

[73] Assignee: Sumitomo Seika Chemicals Co., Ltd., Hyogo, Japan

[21] Appl. No.: 637,155

[22] Filed: Jan. 3, 1991

[30] Foreign Application Priority Data

Jan. 31, 1990 [JP] Japan ................................ 2-22774

[51] Int. Cl.$^5$ .............................................. C08F 2/20
[52] U.S. Cl. ........................................ 526/66; 526/65; 526/73; 526/200; 526/216; 526/303.1; 526/307.2; 526/312; 526/317.1
[58] Field of Search ............... 526/66, 65, 73, 317.1, 526/312, 303.1

[56] References Cited

U.S. PATENT DOCUMENTS

| 4,226,752 | 10/1980 | Erickson | 260/29.6 |
| 4,618,647 | 10/1986 | Fan et al. | 524/801 |
| 4,683,274 | 7/1987 | Nakamura | 526/216 |
| 4,880,886 | 11/1989 | Kondo | 526/80 |
| 4,914,170 | 4/1990 | Chang | 526/240 |

FOREIGN PATENT DOCUMENTS 119078  9/1984  European Pat. Off. .

Primary Examiner—Joseph L. Schofer
Assistant Examiner—Fred Zitomer

[57] ABSTRACT

An improved process for the production of a water-absorbent resin by reversed phase suspension polymerization of a water-soluble ethylenic unsaturated monomer is disclosed. The process is conducted by subjecting an aqueous solution of a water-soluble ethylenic unsaturated monomer to reversed phase suspension polymerization reaction of a first stage in a petroleum hydrocarbon solvent in the presence of a surfactant and/or polymeric protective colloid by using a radical polymerization initiator optionally in the presence of a crosslinking agent, cooling the resulting slurry to precipitate the surfactant and/or polymeric protective colloid, and adding an aqueous solution of a water-soluble ethylenic unsaturated monomer containing a radical polymerization initiator and optionally a crosslinking agent to the first polymerization reaction system to further carry out the reversed phase suspension polymerization reaction, at least, once.

16 Claims, No Drawings

PROCESS FOR PRODUCTION OF WATER-ABSORBENT RESIN

FIELD OF THE INVENTION

The present invention relates to the production of a water-absorbent resin. More particularly, it relates to a process for the production of a water-absorbent resin having properties suitable for water-absorbent materials in the sanitary material field. The water-absorbent resin is cheap and has excellent productivity.

BACKGROUND OF THE INVENTION

Recently, water-absorbent resins have been used in the sanitary field, for example, in menstrual articles, diapers and the like, the agricultural and horticultural fields, for example, in water retention agents, soil conditioning agents and the like and industrial fields, for example, in cutoff materials, anti-dewing agents and the like, and they are useful in various applications. Among these, water-absorbent resins are advantageously used in the sanitary field in menstrual articles, diapers and the like.

One kind of these water-absorbent resins is a polymer which is lightly crosslinked, and examples thereof include hydrolysates of starch-acrylonitrile graft copolymer (Japanese Patent Kokoku No. 49-43395), neutralized products of starch-acrylic acid graft copolymer (Japanese Patent Kokai No. 51-125468), specified products of vinyl acetateacrylic acid ester copolymer (Japanese Patent Kokai No. 52-14689), partially neutralized polyacrylic acid products (Japanese Patent Kokai Nos. 62-172006, 57-158209 and 57-21405) and the like.

Usually, the properties desired for water-absorbent resins are a high absorbency, an excellent water-absorption rate, a high gel strength after absorption of water, a shape suitable for application, conformability to a material to be used therewith and the like. Particularly, the desired properties for water-absorbent resins used for sanitary materials are a high absorbency, a high water-absorption rate, a high gel strength after absorption of water, large particle size, less fine powder, a sharp distribution of particle size, integrity with a pulp, a small amount of reversion of absorbed substances the exterior, excellent diffusion of absorbed substances into interior of the absorbents and the like. It can be said that a good water-absorbent material should satisfy these properties as well as be safe and cheap. Thus, hitherto, water-absorbent resins have been mainly produced by solution polymerization or reversed phase suspension polymerization of water-soluble ethylenic unsaturated monomers. Among these, the production of water-absorbent resins by reversed phase suspension polymerization has following disadvantages.

Firstly, a water-absorbent resin obtained by reversed phase suspension polymerization method of a water-soluble ethylenic unsaturated monomer is powder of spherical particles having a sharp distribution of particle size in comparison with that obtained by subjecting the monomer to solution polymerization, followed by grinding. However, a water-absorbent resin having large particle size cannot obtained. Secondly, since a surfactant and/or a polymeric protective colloid are used, they remain on the surface of a product and therefore initial wettability by water is inferior due to water repellency of the surfactant and/or polymeric protective colloid. As means for mitigating this phenomenon and improving initial wettability by water, it has been considered to remove the surfactant and/or polymeric protective colloid from a product by filtering a slurry obtained by reversed phase suspension polymerization and drying. However, purification of the filtrate is very expensive and such a process is far from an economical production process, although initial wettability by water is improved. Thirdly, the polymerization of a water-soluble ethylenic unsaturated monomer is an exothermic reaction and heat is generated within a short period of time. Therefore, in the reversed phase suspension polymerization, an increase in amount of the monomer in a solvent is limited due to removal of heat. Accordingly, improvement of productivity by decreasing amount of the solvent and increasing the amount of the monomer is limited. Fourthly, in the reversed phase suspension polymerization, the surfactant and/or polymeric protective colloid should be used, at least, in an amount sufficient for making a suspension in order to carry out a stable polymerization, and the amount cannot be reduced to less than this required minimum amount.

OBJECTS OF THE INVENTION

In order to solve the above problems, the present inventors have made a thorough study. As a result, it has been found that, by carrying out the reversed phase suspension polymerization in multiple stages, a water-absorbent resin having large particle size, less fine powder, a sharp distribution and extremely excellent wettability by water in addition to excellent water absorption properties can be obtained, productivity can be greatly improved and further the amount of surfactant and/or polymeric protective colloid used can be reduced. Thus, the present invention been completed.

The main object of the present invention is to provide an improved process for the production of a water-absorbent resin by reversed phase suspension polymerization of a water-soluble ethylenic unsaturated monomer.

This object as well as other objects and advantages of the present invention will be apparent to those skilled in the art from the following description.

SUMMARY OF THE INVENTION

According to the present invention, there is provided a process for the production of a water-absorbent resin by reversed phase suspension polymerization of a water-soluble ethylenic unsaturated monomer comprising subjecting an aqueous solution of a water-soluble ethylenic unsaturated monomer to reversed phase suspension polymerization reaction of a first stage in a petroleum hydrocarbon solvent in the presence of a surfactant and/or polymeric protective colloid by using a radical polymerization initiator optionally in the presence of a crosslinking agent, cooling the resulting slurry to precipitate the surfactant and/or polymeric protective colloid, and adding an aqueous solution of a water-soluble ethylenic unsaturated monomer containing a radical polymerization initiator and optionally a crosslinking agent to the first polymerization reaction system to further carry out the reversed phase suspension polymerization reaction, at least, once.

DETAILED DESCRIPTION OF THE INVENTION

In the process of the present invention, the reversed phase suspension polymerization reaction is carried out in multiple stages of, at least, two stages. Since, usually, the desired result can be obtained by a polymerization reaction of two stages, the two stage reaction is mainly explained below.

That is, according to the process of the present invention, for carrying out the two stage reaction, an aqueous solution of a water-soluble ethylenic unsaturated monomer is firstly polymerized in a petroleum hydrocarbon solvent in the presence of a surfactant and/or polymeric protective colloid by using a radical polymerization initiator optionally in the presence of a crosslinking agent. Then, after polymerization, the resulting slurry solution is cooled so that the surfactant and/or polymeric protective colloid are precipitated in the solvent to prevent an aqueous solution of a monomer for the second stage from forming a suspension. Then, the monomer solution of the second stage is added and absorbed by the water-containing gel produced by the first polymerization and the second polymerization is carried out.

When the monomer solution of the second stage is added to the reaction system under the conditions that the surfactant and/or polymeric protective colloid are dissolved in the solvent after the completion of the first polymerization, the monomer solution is suspended before it is absorbed by the water-containing gel formed in the first polymerization and, therefore, the particle size of the resulting product becomes small and the distribution thereof becomes broad. To the contrary, when the monomer solution of the second stage is added to the reaction system under the conditions that the surfactant and/or polymeric protective colloid are precipitated in the solvent, the water-containing gel obtained by the first polymerization is hardly effected by surface activities of the surfactant and/or polymeric protective colloid and, therefore, a water-absorbent resin having large particle size, less fine powder and a sharp distribution of particle size can be obtained. Further, wettability by water of the resulting water-absorbent resin is remarkably improved. Perhaps, this results from envelopment of the surfactant and/or polymeric protective colloid with the monomer solution of the second stage upon absorption of the solution by the water-containing gel obtained by the first polymerization.

The water-soluble ethylenic unsaturated monomer used may be any of the conventional monomers. Examples thereof include (meth)acrylic acid, 2-(meth)acrylamide-2 methylpropanesulfonic acid and/or alkali salts thereof, nonionic monomers such as (meth)acrylamide, N,N-dimethyl acrylamide, 2-hydroxyethyl(meth)acrylate, N-methylol(meth)acrylamide and the like, amino group-containing unsaturated monomers such as diethylaminoethyl-(meth)acrylate, diethylaminopropyl(meth)acrylate, dimethylaminopropyl(meth)acrylate and the like, and quarternized products thereof. They are used alone or in combination thereof. (The term "(meth)acryl" used herein means both "acryl" and "methacryl".) Among them, acrylic acid, methacrylic acid or alkali salts thereof, acrylamide, methacrylamide, N,N-dimethylacrylamide are preferred. Further, as the monomer component used in the second and subsequent stages may be the same as or different from that used in the first stage. In general, the monomer concentration in the aqueous solution of a water-soluble ethylenic unsaturated monomer is preferably 25% by weight to its saturated solution.

Any surfactant and polymeric protective colloid can be used insofar as the reversed phase suspension polymerization can proceed in the polymerization of the first stage, and they can be used in combination thereof. As the surfactant, for example, there can be used nonionic surfactants such as sorbitan fatty acid ester, polyglycerin fatty acid ester, sucrose fatty acid ester, sorbitol fatty acid ester, polyoxyethylene alkylphenyl ether and the like. As the polymeric protective colloid, for example, there can be used ethyl cellulose, ethyl hydroxyethyl cellulose, oxydized polyethylene, polyethylene modified with maleic anhydride, EPDM (etylene-propylene-diene-terpolymer) modified with maleic anhydride and the like. Further, anionic surfactants such as fatty acid salts, alkyl benzenesulfonate salts, alkyl methyltaurate salts, polyoxyethylene alkylphenyl ether sulfate, polyoxyethylene alkyl ether sulfonate and the like can also be used in combination with the nonionic surfactants and/or polymeric protective colloid.

The amount of these surfactants and/or polymeric protective colloids used is 0.1 to 5% by weight, preferably, 0.2 to 3% by weight based on the total weight of the aqueous monomer solution of the first stage.

The petroleum hydrocarbon solvent used is, for example, selected from the group consisting of aliphatic hydrocarbons, cycloaliphatic hydrocarbons or aromatic hydrocarbons. As aliphatic hydrocarbons, n-pentane, n-hexane, n-heptane, ligroin and the like are preferred. As the cycloaliphatic hydrocarbons, cyclopentane, methylcyclopentane, cyclohexane, methylcyclohexane, and the like are preferred. As the aromatic hydrocarbons, benzene, toluene, xylene and the like are preferred. Particularly, n-hexane, n-heptane, cyclohexane, toluene and xylene can be advantageously used because they are readily available and cheap and are of stable industrial quality.

The crosslinking agent optionally used in the first stage and the second and subsequent stages is that having at least two polymerizable unsaturated groups and/or reactive functional groups. Examples of the crosslinking agent having at least two polymerizable unsaturated groups include di- or tri(meth)acrylate esters of polyols such as ethylene glycol, propylene glycol, trimethylolpropane, glycerin polyoxyethylene glycol, polyoxypropylene glycol, polyglycerin and the like, unsaturated polyesters obtained by reacting the above polyols with unsaturated acids such as maleic acid, fumaric acid and the like, bisacrylamides such as N,N'-methylene bisacrylamide and the like, di- or tri(meth)acrylate esters obtained by reacting polyepoxide with (meth)acrylic acid, di(meth)acrylate carbamyl esters obtained by reacting polyisocyanates such as tolylene diisocyanate, hexamethylene diisocyanate and the like with hydroxyethyl (meth)acrylate, allylated starch, allylated cellulose, diallyl phthalate, N,N',N"-triallyl isocyanurate, divinylbenzene and the like.

Among them, ethylene glycol diacrylate, ethylene glycol dimethacrylate, diethylene glycol diacrylate, diethylene glycol dimethacrylate, propylene glycol diacrylate, propylene glycol dimethacrylate, polyethylene glycol diacrylate, polyethylene glycol dimethacrylate, diallyl phthalate, N,N',N"-triallyl isocyanate, N,N'-methylene bisacrylamide and the like are usually used.

The crosslinking agent having at least two reactive functional groups is, for example, selected from the group consisting of diglycidyl ether compounds, haloepoxy compounds, isocyanate compounds and the like. Among them, particularly, the diglycidyl ether compound is suitable. Examples of the diglycidyl ether include (poly)ethylene glycol diglycidyl ether, (poly)propylene glycol glycidyl ether, (poly)glycerin glycidyl ether and the like. Among them, ethylene glycol diglycidyl ether provides most preferred results. (The term "(poly)ethylene glycol" used herein means both "ethylene glycol" and "polyethylene glycol"). Further, examples of the haloepoxy compound include epichlorohydrin, epibromohydrin, α-methylepichlorohydrin and the like and examples of the isocyanate compound include 2,4-tolylene diisocyanate, hexamethylene diisocyanate and the like. Any of these compounds can be used in the present invention. In general, the crosslinking agent is used in an amount of 0.001 to 5% by weight based on the weight of the monomer.

As the radical polymerization initiator used, conventional water-soluble radical polymerization initiators such as potassium persulfate, ammonium persulfate, sodium persulfate and the like are suitable and these can be used in combination with sulfite and the like as a redox initiator. However, in the case of using an oil-soluble radical polymerization initiator, since the resulting polymer generally becomes water-soluble, it should be used in the presence of the crosslinking agent. In this case, oil-soluble initiators such as benzoyl peroxide, azobisisobutyronitrile and the like are suitable. It is preferred to use the radical polymerization initiator in an amount ranging from 0.005 to 1.0 mol % based on the monomer. When the amount is less than 0.005 mol %, it takes a very long time to carry out the polymerization reaction and, when the amount exceeds 1.0 mol %, a rapid polymerization reaction is caused and it is dangerous.

The polymerization temperature varies depending upon the polymerization initiator to be used. The polymerization temperature is usually 20° to 110° C. preferably, 40° to 80° C. When the polymerization is carried out at a temperature of higher than 110° C. it is difficult to remove the heat of polymerization and, therefore, the polymerization cannot be carried out smoothly. When the polymerization is carried out at a temperature of lower than 20° C., the polymerization rate is lowered and a long polymerization time is required. This is not preferred from an economical viewpoint.

Precipitation of the surfactant and/or polymeric protective colloid after the polymerization of the first stage, which is one of the characteristics of the present invention, is carried out by cooling the reaction system. The cooling temperature varies depending upon the surfactant and polymeric protective colloid used as well as the kind of solvent. For example, in the case of hexaglyceryl monobehenylate and n-heptane, the temperature is 38° to 40° C. In the case of hexaglyceryl monobehenylate and cyclohexane, the temperature is 27° to 30° C. and, in the case of sorbitan monostearate and n-heptane, the temperature is 29° to 31° C.

The amount of the aqueous solution of the water-soluble ethylenic monomer containing the radical polymerization initiator and optionally the crosslinking agent used in the second and subsequent stages, which is absorbed by the water-containing gel obtained by the polymerization of the first stage, is 50 to 300% by weight based on the total weight of the aqueous water-soluble ethylenic unsaturated monomer solution of the first stage.

When the amount of the aqueous solution of water-soluble ethylenic unsaturated monomer of the second and subsequent stages is less than 50% by weight, the desired various advantages of the present invention are barely realized. On the other hand, when the amount is more than 300% by weight, the monomer solution is not completely absorbed during absorption of the second and subsequent stages and this is undesirable because it forms a mass or extremely large coarse particles.

The following Examples further illustrate the present invention in detail but are not to be construed to limit the scope thereof.

In each Example, physical properties of the water-absorbent resin were determined according to the following methods.

(1) Absorbency

A water-absorbent resin (1 g) was dispersed in a 0.9% (w/w) aqueous solution of sodium chloride (200 ml), thoroughly swollen and then filtered through a 200 mesh metal wire net. The resulting swollen resin was weighed and the weight was taken as the absorbency.

(2) Water-Absorption Rate (Wettability)

A water-absorbent resin (5 g) was spread to a range of about 3.5 cm$\phi$ in a Petri dish. Then, a 0.9% (w/w) aqueous solution of sodium chloride (2 cc) was added dropwise to this by a pipette and the period of time required for complete absorption of water was measured and the time was taken as the water wettability.

(3) Integrity With a Pulp (Evaluation of Integrity With a Carrier Pulp for Using the Resin as an Adsorbent)

A filter paper of 11 cm$\phi$ was placed on a Petri dish and water (2 cc) was absorbed by the filter paper. A water-absorbent resin (2 g) was uniformly scattered on the filter paper. Then, the Petri dish was dried at 60° C. for one hour and the amount of the water-absorbent resin adhered to the filter paper was measured and the amount was taken as the integrity.

(4) Measurement of Reversion and Diffusion

A water-absorbent resin (5 g) was uniformly scattered on a pulp sheet having the weight of 100 g/m$^2$ which was cut out in a size of 40 cm × 14 cm. The same pulp sheet as described above was laminated thereon and pressed by uniformly applying a pressure at 2 kg/cm$^2$ on the entire pulp surface to obtain an absorbent.

1.6% (w/w) Aqueous solution of sodium chloride (150 ml) was poured on the center part of the absorbent thus prepared over 1 minute and the absorbent was allowed to stand for 10 minutes. Then, 20 sheets of filter paper (No. 2, manufactured by Toyo Roshi Co., Ltd.) cut out in a size of 10 cm × 10 cm were placed on the center part and pressed by placing a weight 3.5 kg (bottom surface area: 10 cm × 10 cm) thereon. The amount of liquid reverted was determined by measuring the amount of liquid absorbed in the filter paper.

Further, diffusion length was determined by measuring spreading of the aqueous solution of sodium chloride.

EXAMPLE 1

N-heptane (550 ml) was placed in a 1 liter four necked cylindrical round bottom flask equipped with a stirrer, a reflux condenser, a dropping funnel and a nitrogen gas inlet. To the flask was added hexaglyceryl monobehenylate having, an HLB of 13.1 (manufactured and sold by Nippon Oil and Fats Co., Ltd. under the trade name of Nonion GV-106) (1.38 g). The surfactant was dissolved by heating at 50° C. and the mixture was cooled to 30° C. Separately, a 80% (w/w) aqueous solution of acrylic acid (92 g) was placed in a 500 ml conical flask and 20.1% (w/w) aqueous solution of sodium hydroxide (152.6 g) was added dropwise with external ice-cooling to neutralize 75 mol % of the acrylic acid. To the mixture was added potassium persulfate (0.11 g). The resulting partially neutralized acrylic acid solution was added to the above four necked round bottom flask and the reaction system was thoroughly purged with nitrogen gas. The reaction system was heated to carry out the polymerization reaction of the first stage, while maintaining the bath temperature at 70° C. The resulting polymerization slurry solution was cooled to 20° C. and the same amount of the partially neutralized acrylic acid solution prepared according to the same manner as described above was added dropwise to the reaction system and allowed to absorb for 30 minutes. At the same time, the system was thoroughly purged with nitrogen gas. The system was heated and subjected to polymerization of the second stage, while maintaining the bath temperature at 70° C. Water and n-heptane were distilled off and the residue was dried to obtain a water-absorbent resin (192.0 g) containing no fine powder and having a sharp distribution of particle size.

EXAMPLE 2

According to the same manner as described in Example 1, the polymerization was carried out except that ethylene glycol diglycidyl ether (each 18.4 mg) was added as a crosslinking agent to the partially neutralized aqueous acrylic acid solution used in polymerization of the first and second stages to obtain a water-absorbent resin (192.5 g) containing no fine powder and having a sharp distribution of particle size.

EXAMPLE 3

According to the same manner as described in Example 1, the polymerization was carried out except that the temperature in the system was adjusted to 25° C. upon absorption of the partially neutralized aqueous acrylic acid solution used in polymerization of the second stage to the polymerization solution of the first stage by obtain a water-absorbent resin (192.8 g) containing no fine powder and having a sharp distribution of particle size.

EXAMPLE 4

According to the same manner as described in Example 2, the polymerization was carried out except that 37% (w/w) aqueous solution of acrylamide (196.2 g) was used in place of the partially neutralized aqueous acrylic acid solution used in the polymerization of the second stage to obtain a water-absorbent resin (173.1 g) containing no fine powder and having a sharp distribution of particle size.

EXAMPLE 5

According to the same manner as described in Example 2, the polymerization was carried out except that an aqueous monomer solution prepared by mixing a partially neutralized aqueous acrylic acid solution, which was obtained by mixing 80% (w/w) aqueous solution of acrylic acid (46 g) and 14.6% (w/w) aqueous solution of sodium hydroxide (104.8 g) to neutralize 75 mol % of the acrylic acid, and 30% (w/w) aqueous solution of acrylamide (120.9 g) was used for the polymerization of the first and second stages, respectively, in place of the partially neutralized aqueous acrylic acid solution used for the polymerization of the first and second stages to obtain a water-absorbent resin (172.5 g) containing no fine powder and having a sharp distribution of particle size.

EXAMPLE 6

According to the same manner as described in Example 1, the polymerization was carried out except that sorbitan monostearate having an HLB of 4.7 (manufactured and sold by Nippon Oil and Fats Co., Ltd. under the trade name of Nonion SP-60R) (2.76 g) was used in place of hexaglyceryl monobehenylate having an HLB of 13.1 (manufactured and sold by Nippon Oil and Fats Co., Ltd. under the trade name of Nonion GV-106) (1.38 g) and the temperature in the system was adjusted to 15° C. upon the absorption of the partially neutralized acrylic acid solution used in the polymerization of the second stage to the polymerization solution of the first stage to obtain a water-absorbent resin (194.0 g) containing no fine powder and having a sharp distribution of particle size.

EXAMPLE 7

According to the same manner as described in Example 1, the polymerization was carried out except that sorbitan monolaurate having an HLB of 8.6 (manufactured and sold by Nippon Oil and Fats Co., Ltd., Japan under the trade name of Nonion LP-20R) (0.97 g) was used in place of hexaglyceryl monobehenylate having an HLB of 13.1 (manufactured and sold by Nippon Oil and Fats Co., Ltd. under the trade name of Nonion GV-106) (1.38 g), the partially neutralized aqueous acrylic acid solution used for the polymerization of the second stage was prepared by mixing 80% (w/w) aqueous solution of acrylic acid (46 g) and 20.1% (w/w) aqueous solution of sodium hydroxide (76.3 g) to neutralize 75 mol % of the acrylic acid, and the temperature in the system was adjusted to 10° C. upon the absorption of the monomer solution to the polymerization solution of the first stage to obtain a water-absorbent resin (143.9 g) containing no fine powder and having a sharp distribution of particle size.

EXAMPLE 8

According to the same manner as described in Example 2, the polymerization was carried out except that a modified polyethylene wherein anhydrous maleic acid was added (manufactured and sold by Mitsui Petrochemical Industries Co., Ltd. under the trade name of Hi-wax 1105A) (2.76 g) was used in place of hexaglyceryl monobehenylate having an HLB of 13.1 (manufactured and sold by Nippon Oil and Fats Co., Ltd. under the trade name of Nonion GV-106) (1.38 g) to obtain a water-absorbent resin (193.4 g) containing no fine powder and having a sharp distribution of particle size.

EXAMPLE 9

According to the same manner as described in Example 1, the polymerization was carried out except that sucrose di-tristearate having an HLB of 3.0 (manufactured and sold by Mitsubishi Chemical Food Industries Co., Ltd. under the trade name of Sugar Ester S-370) (1.38 g) was used in place of hexaglyceryl monobehenylate having an HLB of 13.1 (manufactured and sold by Nippon Oil and Fats Co., Ltd. under the trade name of Nonion GV-106) (1.38 g) to obtain a water-absorbent resin (190.7 g) having no fine powder and a sharp distribution of particle size.

EXAMPLE 10

According to the same manner as described in Example 1, the polymerization was carried out except that ethyl cellulose (manufactured and sold by Heracules Co., Ltd. under the trade name of Ethyl Cellulose N-22) (2.76 g) was used in place of hexaglyceryl monobehenylate having an HLB of 13.1 (manufactured and sold by Nippon Oil and Fats Co., Ltd. under the trade name of Nonion GV-106) (1.38 g), cyclohexane was used in place of n-heptane as the solvent, and the temperature in the system was adjusted to 10° C. upon the absorption of a partially neutralized acrylic acid solution used in the polymerization of the second stage by the polymerization solution of the first stage to obtain a water-absorbent resin (193.2 g) having no fine powder and a sharp distribution of particle size.

EXAMPLE 11

According to the same manner as described in Example 9, the polymerization was carried out except that a partially neutralized acrylic acid solution used for the polymerization of the second stage was prepared by mixing a 80% (w/w) aqueous solution of acrylic acid (184 g) and a 20.1% (w/w) aqueous solution of sodium hydroxide (305.2 g) to neutralize 75 mol % of the acrylic acid and then potassium persulfate was added thereto to obtain a water-absorbent resin (287.0 g) having no fine powder and a sharp distribution of particle size.

EXAMPLE 12

According to the same manner as described in Example 9, the polymerization was carried out except that polyethylene (n=14) glycol diacrylate (each 27.6 mg) was added as a crosslinking agent to both partially neutralized acrylic acid solutions used for both polymerizations of the first and the second stage to obtain a water-absorbent resin (191.3 g) having no fine powder and a sharp distribution of particle size.

EXAMPLE 13

According to the same manner as described in Example 9, the polymerization was carried out except that N,N'-methylene bisacrylamide (each 18.4 mg) was added as a crosslinking agent for both partially neutralized acrylic acid solutions used for the polymerization of the first and the second stages to obtain a water-absorbent resin (192.6 g) having no fine powder and a sharp distribution of particle size.

EXAMPLE 14

According to the same manner as described in Example 2, the polymerization was carried out except that 28% (w/w) aqueous solution of methacrylamide (310.7 g) was used in place of the partially neutralized acrylic acid solution used for the polymerization of the second stage to obtain a water-absorbent resin (188.5 g) having no fine powder and a sharp distribution of particle size.

EXAMPLE 15

According to the same manner as described in Example 13, the polymerization was carried out except that 25% (w/w) aqueous solution of N,N-dimethylacrylamide (404.8 g) was used in place of the partially neutralized acrylic acid solution used for the polymerization of the second stage to obtain a water-absorbent resin (203.3 g) having no fine powder and a sharp distribution of particle size.

EXAMPLE 16

According to the same manner as described in Example 2, the polymerization was carried out except that 30% (w/w) aqueous solution of acrylamide (242 g) was used in place of the partially neutralized acrylic acid solution used for the polymerization of the first stage and N,N'-methylene bisacrylamide (each 18.4 mg) was used in place of ethylene glycol diglycidyl ether used for both polymerizations of the first and second stages to obtain a water-absorbent resin (172.9 g) having no fine powder and a sharp distribution of particle size.

EXAMPLE 17

According to the same manner as described in Example 2, the polymerization was carried out except that hexaglyceryl monobehenylate having an HLB of 13.1 (manufactured and sold by Nippon Oil and Fats Co., Ltd. under the trade name of Nonion GV-106) (0.92 g) was used in combination with a modified polyethylene wherein anhydrous maleic acid was added (manufactured and sold by Mitsui Petrochemical Industries Co., Ltd. under the trade name of Hi-wax 1105A) (0.92 g) and the temperature in the system was adjusted to 30° C. upon absorption of the partially neutralized acrylic acid solution used for the polymerization of the second stage to the polymerization solution of the first stage by obtain a water-absorbent resin (192.4 g) having no fine powder and a sharp distribution of particle size.

EXAMPLE 18

After completion of the polymerization of the second stage according to Example 1, the resulting polymerization slurry solution was cooled to 20° C. Separately, 80% (w/w) aqueous solution of acrylic acid (92 g) and 20.1% (w/w) aqueous solution of sodium hydroxide (152.6 g) were mixed to neutralize 75 mol % of the acrylic acid. To the mixture was added ethylene glycol diglycidyl ether (36.8 g) and further added potassium persulfate (0.11 g). The resulting partially neutralized acrylic acid solution was added dropwise to the above reaction system and absorbed for 30 minutes. At the same time, the reaction system was thoroughly purged with nitrogen gas. The system was heated and subjected to the polymerization of a third stage, while maintaining the bath temperature at 70° C.

Water and n-heptane were distilled off and the residue was dried to obtain a water-absorbent resin (287.5 g) having no fine powder and a sharp distribution of particle size.

COMPARATIVE EXAMPLE 1

N-heptane (550 ml) was placed in a 1 liter four necked cylindrical round bottom flask equipped with a stirrer, a reflux condenser, a dropping funnel and a nitrogen gas inlet. To the flask was added hexaglyceryl monobehenylate having an HLB of 13.1 (manufactured and sold by Nippon Oil and Fats Co., Ltd. under the trade name of Nonion GV-106) (1.38 g). After heating at 50° C. to dissolve the surfactant, the mixture was cooled to 30° C. Separately, 80% (w/w) aqueous solution of acrylic acid (92 g) was placed in a 500 ml conical flask and 20.1% (w/w) aqueous solution of sodium hydroxide (152.6 g) was added dropwise with external ice-cooling to neutralize 75 mol % of the acrylic acid. Potassium persulfate (0.11 g) was added to the mixture and dissolved.

The resulting partially neutralized acrylic acid solution was added to the above four necked round bottom flask and the reaction system was thoroughly purged with nitrogen gas. The reaction system was heated and subjected to the polymerization reaction, while maintaining the bath temperature at 70° C. Water and n-heptane were distilled off and the residue was dried to obtain a water-absorbent resin (96.7 g).

COMPARATIVE EXAMPLE 2

According to the same manner as described in Comparative Example 1, the polymerization was carried out except that sorbitan monostearate having an HLB of 4.7 (manufactured and sold by Nippon Oil and Fats Co., Ltd. under the trade name of Nonion SP-60R) (2.76 g) was used in place of hexaglyceryl monobehenylate having, an HLB of 13.1 (manufactured and sold by Nippon Oil and Fats Co., Ltd. under the trade name of Nonion GV-106) (1.38 g) to obtain a water-absorbent resin (98.2 g).

COMPARATIVE EXAMPLE 3

According to the same manner as described in Comparative Example 1, the polymerization was carried out except that sorbitan monolaurate having an HLB of 8.6 (manufactured and sold by Nippon Oil and Fats Co., Ltd. under the trade name of Nonion LP-20R) (0.97 g) was used in place of hexaglyceryl monobehenylate having an HLB of 13.1 (manufactured and sold by Nippon Oil and Fats Co., Ltd. under the trade name of Nonion GV-106) (1.38 g) to obtain a water-absorbent resin (96.0 g).

COMPARATIVE EXAMPLE 4

According to the same manner as described in Comparative Example 1, the polymerization was carried out except that modified polyethylene wherein anhydrous maleic acid was added (manufactured and sold by Mitsui Petrochemical Industries Co., Ltd. under the trade name of Hi-wax 1105A) (2.76 g) was used in place of hexaglyceryl monobehenylate having an HLB of 13.1 (manufactured and sold by Nippon Oil and Fats Co., Ltd. under the trade name of Nonion GV-106) (1.38 g) to obtain a water-absorbent resin (98.0 g).

COMPARATIVE EXAMPLE 5

According to the same manner as described in Comparative Example 1, the polymerization was carried out except that sucrose di-tristearate having an HLB of 3.0 (manufactured and sold by Mitsubishi Chemical Food Industries Co., Ltd. under the trade name of Sugar Ester S-370) (1.38 g) was used in place of hexaglyceryl monobehenylate having an HLB of 13.1 (manufactured and sold by Nippon Oil and Fats Co., Ltd. under the trade name of Nonion GV-106) (1.38 g) to obtain a water-absorbent resin (97.1 g).

COMPARATIVE EXAMPLE 6

According to the same manner as described in Comparative Example 1, the polymerization was carried out except that ethyl cellulose (manufactured and sold by Heracules Co., Ltd. under the trade name of Ethyl Cellulose N-22) (2.76 g) was used in place of hexaglyceryl monobehenylate having an HLB of 13.1 (manufactured and sold by Nippon Oil and Fats Co., Ltd. under the trade name of Nonion GV-106) (1.38 g) and cyclohexane was used in place of n-heptane to obtain a water-absorbent resin (98.2 g).

COMPARATIVE EXAMPLE 7

According to the same manner as described in Examples 1, the polymerization was carried out except that the temperature in the system was adjusted to 45° C. upon absorption of the partially neutralized acrylic acid solution used for the polymerization of the second stage by the polymerization solution of the first stage to obtain a water-absorbent resin (192.5 g).

Properties of water-absorbent resins obtained in the above Examples and Comparative Examples are shown in Table 1 below.

TABLE 1

|  | Absorbency (g/g) | Water-absorption rate (wettability) (sec.) | Integrity (%) | Reversion (g) | Diffusion (cm) | Average particle size (μm) | Fine powder F100 μm (%) |
|---|---|---|---|---|---|---|---|
| Ex. 1 | 70 | 5 | 92 | 0.5 | 30 | 450 | 0.1 |
| Ex. 2 | 55 | 4 | 85 | 0.2 | 29 | 420 | 0.3 |
| Ex. 3 | 72 | 5 | 93 | 0.7 | 33 | 520 | 0.0 |
| Ex. 4 | 50 | 6 | 78 | 1.0 | 28 | 370 | 1.1 |
| Ex. 5 | 48 | 6 | 74 | 1.8 | 27 | 390 | 0.9 |
| Ex. 6 | 69 | 9 | 70 | 3.3 | 27 | 310 | 12.1 |
| Ex. 7 | 75 | 2 | 90 | 4.0 | 26 | 340 | 5.1 |
| Ex. 8 | 58 | 6 | 83 | 0.3 | 32 | 600 | 0.0 |
| Ex. 9 | 71 | 5 | 90 | 0.7 | 28 | 400 | 0.4 |
| Ex. 10 | 68 | 3 | 94 | 0.6 | 29 | 390 | 2.1 |
| Ex. 11 | 67 | 3 | 92 | 0.5 | 30 | 490 | 0.6 |
| Ex. 12 | 54 | 4 | 87 | 0.6 | 27 | 360 | 1.3 |
| Ex. 13 | 59 | 4 | 89 | 0.4 | 28 | 380 | 0.8 |
| Ex. 14 | 49 | 4 | 77 | 1.5 | 26 | 320 | 2.3 |
| Ex. 15 | 50 | 4 | 78 | 0.8 | 26 | 310 | 2.7 |
| Ex. 16 | 52 | 5 | 83 | 0.9 | 27 | 410 | 0.8 |
| Ex. 17 | 56 | 4 | 83 | 0.3 | 30 | 370 | 1.3 |
| Ex. 18 | 67 | 3 | 90 | 0.4 | 30 | 470 | 0.2 |
| Comp. Ex. 1 | 72 | 25 | 43 | 4.5 | 25 | 200 | 12 |
| Comp. Ex. 2 | 70 | 30 | 35 | 7.4 | 22 | 95 | 69.3 |
| Comp. Ex. 3 | 75 | 8 | 68 | 15.9 | 18 | 250 | 15 |
| Comp. Ex. 4 | 81 | 35 | 47 | 5.5 | 23 | 260 | 14 |
| Comp. Ex. 5 | 73 | 29 | 38 | 5.0 | 21 | 190 | 26 |
| Comp. | 74 | 12 | 69 | 4.7 | 24 | 270 | 7 |

TABLE 1-continued

|  | Absorbency (g/g) | Water-absorption rate (wettability) (sec.) | Integrity (%) | Reversion (g) | Diffusion (cm) | Average particle size (μm) | Fine powder F100 μm (%) |
|---|---|---|---|---|---|---|---|
| Ex. 6 Comp. Ex. 7 | 70 | 7 | 71 | 5.1 | 23 | 195 | 17 |

The water-absorbent resin obtained by the process of the present invention is suitable for the sanitary field, the soil conditioning field and the industrial field and the like, particularly, for the sanitary field. That is, since the water-absorbent resin obtained by the process of the present invention has large particle size, less fine powder and a sharp distribution of particle size, it has the following advantages. Firstly, in diaper and the like, reversion is inhibited and diffusion of a substance absorbed occurs nicely. Secondly, in the case of fixing the water-absorbent resin in a pulp, the water-absorbent resin hardly falls off and a good absorbent article can be obtained. Thirdly, in the case of spreading the water-absorbent resin with a spreader, non-uniform spreading is prevented and it is easy to maintain a constant spread. Further, since the amount of the surfactant or polymeric protective colloid in the surface layer of the water-absorbent resin is little, the initial water-absorption rate, i.e., wettability is improved. Furthermore, in the case of fixing the water-absorbent resin to a pulp, integrity of the water-absorbent resin with the pulp is improved and the absorbent article wherein the resin is hardly falls off is obtained. In addition, since productivity is improved, a cheap water-absorbent resin can be provided. As described hereinabove, the water-absorbent resin obtained by the process of the present invention has excellent properties in, particularly, the sanitary field because of its various advantages.

What is claimed is:

1. A process for the production of water-absorbent resin by reversed phase suspension polymerization of a water-soluble ethylenic unsaturated monomer, which comprises the steps of:
   A. subjecting an aqueous solution of the water-soluble ethylenic unsaturated monomer to a reversed phase suspension polymerization reaction of a first stage in a petroleum hydrocarbon solvent in the presence of a surfactant and/or polymeric protective colloid by using a radical polymerization initiator optionally in the presence of a crosslinking agent,
   B. cooling the solution to precipitate the surfactant and/or polymeric protective colloid,
   C. adding an aqueous solution of a water soluble-ethylenic unsaturated monomer solution containing a radical polymerization initiator and optionally a crosslinking agent to the first polymerization reaction system to absorb it on gel formed in the first polymerization reaction,
   D. then, heating the reaction mixture to carry out a second reversed phase suspension polymerization reaction, and
   E. optionally, repeating the above steps B, C, D at least once.

2. A process according to claim 1, wherein the reversed phase suspension polymerization reaction is carried out in two stages and the aqueous solution of the water-soluble ethylenic unsaturated monomer solution containing the radical polymerization initiator and optionally the crosslinking agent used in the step C is added to the polymerization system of the first stage in a ratio of 50 to 300% by weight based on the weight of the monomer solution used in the step A.

3. A process according to claim 1, wherein the water-soluble ethylenic unsaturated monomer component used in the step C is the same as or different from the monomer component used in step A.

4. A process according to claim 1, wherein the water-soluble ethylenic unsaturated monomer is acrylic acid, methacrylic acid or an alkali salt thereof.

5. A process according to claim 1, wherein the water-soluble ethylenic unsaturated monomer is acrylamide, methacrylamide or N,N-dimethylacrylamide.

6. A process according to claim 1, wherein the surfactant is a nonionic surfactant, or a combination of a nonionic surfactant and an anionic surfactant.

7. A process according to claim 6, wherein the surfactant is one or more members selected from the group consisting of sorbitan fatty acid esters, polyglycerin fatty acid esters, sucrose fatty acid esters and sorbitol fatty acid esters.

8. A process according to claim 1, wherein the polymeric protective colloid is one or more members selected from the group consisting of ethyl cellulose, ethyl hydroxyethyl cellulose, oxydized polyethylene, polyethylene modified with maleic anhydride, polybutadiene modified with maleic anhydride and ethylene-propylene-diene-terpolymer modified with maleic anhydride.

9. A process according to claim 1, wherein the petroleum hydrocarbon solvent is one or more members selected from the group consisting of n-hexane, n-heptane, cyclohexane, toluene and xylene.

10. A process according to claim 1, wherein the aqueous solution of water-soluble ethylenic unsaturated monomer used in each stage contains the monomer in a concentration of not less than 25% by weight.

11. A process according to claim 9, wherein the petroleum hydrocarbon solvent is n-heptane.

12. A process according to claim 1, wherein the radical polymerization initiator is potassium persulfate.

13. A process according to claim 1, wherein the crosslinking agent is ethylene glycol diglycidyl ether or polyethylene glycol diglycidyl ether.

14. A process according to claim 1, wherein the crosslinking agent is ethylene glycol diacrylate, ethylene glycol dimethacrylate, polyethylene glycol diacrylate or polyethylene glycol dimethacrylate.

15. A process according to claim 1, wherein the crosslinking agent is N,N'-methylene bisacrylamide.

16. A process according to claim 1, wherein the reversed phase suspension polymerization reaction is carried out in three or more stages.

* * * * *